United States Patent
Wagner

(10) Patent No.: US 7,250,847 B2
(45) Date of Patent: Jul. 31, 2007

(54) PORTABLE SURFACE MEMBER FOR CONDUCTING EXERCISES OF INDIVIDUALS

(76) Inventor: Michelle A. Wagner, 4371 Beverly Dr., Toledo, OH (US) 43614

( * ) Notice: Subject to any disclaimer, the term of this patent is extended or adjusted under 35 U.S.C. 154(b) by 219 days.

(21) Appl. No.: 10/624,702

(22) Filed: Jul. 23, 2003

(65) Prior Publication Data

US 2005/0016105 A1 Jan. 27, 2005

(51) Int. Cl.
*H04Q 5/22* (2006.01)
(52) U.S. Cl. .................. 340/10.1; 340/568.6; 340/540; 340/515; 340/517; 340/524; 340/426.25; 482/8; 482/4; 482/5
(58) Field of Classification Search .............. 340/10.1, 340/568.6, 540, 515, 517, 524, 426.25; 482/8, 482/4, 5
See application file for complete search history.

(56) References Cited

U.S. PATENT DOCUMENTS

| | | | | |
|---|---|---|---|---|
| 3,641,601 A | * | 2/1972 | Sieg ............................... 5/420 |
| 3,894,437 A | * | 7/1975 | Hagy et al. ................. 73/865.4 |
| 4,522,861 A | * | 6/1985 | Dunsworth .................. 428/192 |
| 5,144,847 A | * | 9/1992 | Furtmayer ............. 73/862.625 |
| 5,186,062 A | * | 2/1993 | Roost ......................... 73/865.4 |
| 6,110,073 A | * | 8/2000 | Saur et al. ...................... 482/8 |
| 6,378,540 B2 | * | 4/2002 | Iwasa ........................... 135/65 |

\* cited by examiner

*Primary Examiner*—Brian Zimmerman
*Assistant Examiner*—Vernal Brown

(57) ABSTRACT

The concept herein is focused on a portable structure, generally in the form of a portable mat or other similar member, that can be moved or transported from place to place to be used in a temporary manner and placed on the ground for use in the process of facilitating the implementation of field exercise tests of individuals who are suspected of criminal or other activity such as driving under the influence of alcohol, such mat comprising in general a flat flexible mat-like member that can be placed flush against the ground for temporary use, such mat having an upper surface with demarcations thereon for guiding a person walking over the upper surface of the mat.

1 Claim, 4 Drawing Sheets

PORTABLE SURFACE MEMBER FOR CONDUCTING EXERCISES OF INDIVIDUALS

D. DISCUSSION OF PRIOR ART

The subject invention relates to the category of devices that are used in conjunction with exercises, and more specifically to help facilitate and/or gauge the performance of standard exercise or maneuvers. The particularized focus of the invention herein is directed to such a device generally described above intended to be used in conducting physical exercise testing procedures used by law enforcement officers to ascertain whether a suspect is physically affected by alcohol or drugs. Mainly such testing procedures are used in conjunction with apprehensions of individuals suspected of driving under the influence of alcohol or drugs. However, there are other potential criminal actions in which the status of an individual's blood alcohol level and/or drug level is of significant importance.

In light of the above, under circumstances where a law enforcement officer has what is termed reasonable suspicion that an individual is or was driving or engaged in other criminal activity while under the influence of alcohol, the legally sanctioned procedure is to request the suspected individual to undergo one or more field sobriety tests. Generally, these field sobriety tests are physical exercises that can be usually or otherwise monitored by the law enforcement officer to determine the individual's relative physical and inter-connected mental and coordination abilities. This is done to ascertain the resultant effects of alcohol and/or drugs on the physical and mental coordination abilities or the suspected individual.

The general array of such tests conventionally include tests such as a finger-to-nose touching exercise to ascertain the manual dexterity, or standing on one foot for a duration, and other physical or mental exercises. One of the frequently used physical tests is one that requires the individual to walk along a marked or imaginary straight line to provide physical evidence of the individual's ability to walk along a straight line. To implement this test, law enforcement officers frequently have the test conducted at on or near a roadway, once an individual's vehicle has been stopped. Not infrequently the officer will use the edge of the pavement, adjacent to the roadway berm as a guiding line for the individual to walk. More frequently, however, the officer will have the individual walk the marked or imaginary line on the roadway berm. This latter area as used for this walking test is more frequently used to avoid placing the individual in the middle or near the paved roadway to avoid the potential of being struck by an oncoming vehicle.

Some of the problems encountered when using a soft berm in this respect centers around the fact that the berm surface is often soft or uneven and other than level, and these problems do indeed cause difficulties for a person attempting to walk along a line on such a surface. For instance, if the berm surface is composed in part of large stones, which is not uncommon, it makes it difficult to walk on such surface, let alone walk straight and evenly. Moreover, if the surface is uneven with a downward slope away from the roadway, which is also fairly common, the walking process is rendered difficult by such fact.

These later described problems that lead to difficulty in walking on such described surfaces give rise to frequent complaints by the individual and defense attorneys that the specifically administered walking test is fallacious and faulty by reason of one or more of the above described surface characteristics. Alternatively stated, the individual involved often argues that he or she was unable to negotiate a fairly conducted walk because the surface used was not conducive to any individual, sober or otherwise, to satisfactorily walk a straight line.

What generally occurs under such circumstances, is that the individual's legal counsel challenges the admissibility of the officer's observations of such walking tests. In a criminal or other proceedings, the challenge seeks to disallow such observation in evidence. Often the challenge may have significant merit, contending that an individual not under the influence of drugs or alcohol would have some difficulty walking along such a surface. Responsive to such challenges it is not unusual for a court of law to uphold such challenges as to this specific field test.

As a result of the foregoing circumstances, this invention herein, as incorporated in a specific physical structure, is conceived as a device to overcome such stated problems. Accordingly, the following objects of the subject invention are directed accordingly.

E. OBJECTS OF INVENTION

It is an object of the subject invention to provide a device that helps law enforcement officers, or others, implementing physical testing of individuals in conjunction with suspected criminal activity;

Another object of the subject invention is to provide an improved device on which an individual can conduct physical exercises or maneuvers;

Yet another object of the subject invention is to provide an improved mat structure which can be used for a person to walk on for conducting field sobriety tests for individuals suspected of being under the influence of drugs and/or alcohol;

Still another object of the subject invention is to provide an improved apparatus to permit an individual to fairly complete a straight walking maneuver for determining the individual's relative coordination abilities;

A further object of the subject invention is to provide an apparatus having a smooth and even surface that will permit an individual to complete a walking maneuver for third party observation;

Other and further objects of the subject invention will become manifest from a reading of the description in conjunction with the drawings.

F. BRIEF DESCRIPTION OF DRAWINGS

G. DESCRIPTION OF GENERAL EMBODIMENT AND SUMMARY OF THE INVENTION

Figure 1:
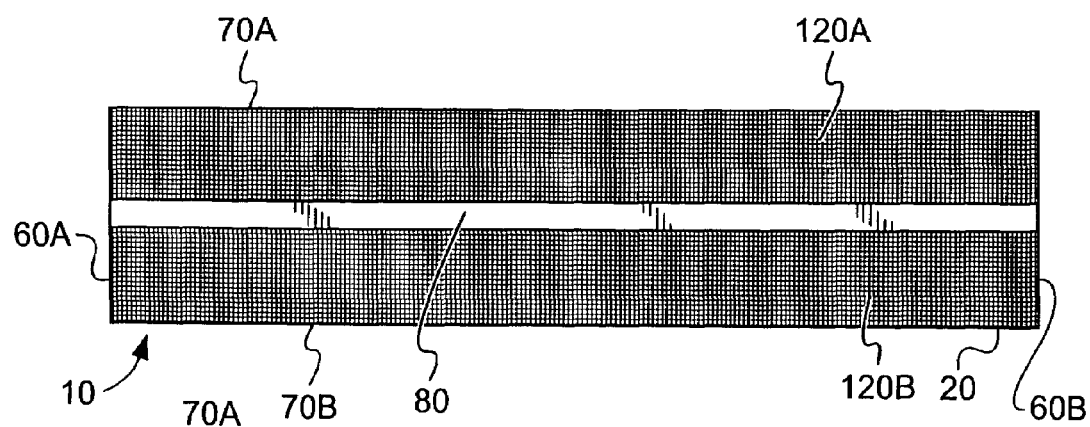
FIG. 1 is a top elevational view of a preferred of the subject invention.

The subject invention is a portable structure, generally in the form of a portable mat or other similar member, that can be moved or transported from place to place to be used in a temporary manner and placed on the ground for use in the process of facilitating the implementation of field exercise tests of individuals who are suspected of criminal or other activity, such mat comprising in general a flat flexible mat-like member that can be placed flush against the ground for temporary use, such mat having an upper surface with demarcations thereon for guiding the user in such exercises.

In a general and overall summary, the subject invention is embodied and otherwise focused on a portable mat member, optimally of a flexible composition and nature, wherein such flexible mat member is used as a smooth, safe, and even surface over which individuals can walk to demonstrate relative physical coordination abilities. As discussed above, the primary application of such a portable mat would be directed to instances where an individual's walking abilities and related coordination can be consummated and observed by a law enforcement officer who suspects that a person is under the influence of alcohol and/or drugs to the degree by which such person's physical and interrelated mental abilities are impaired. It is noted at this juncture that the application of this invention may be used for other circumstances other than law enforcement aspects.

In the most general form of the physical embodiment of the subject invention, the portable mat is a longitudinally extending member wherein it is optimally and easily folded or rolled up for compact storage in a vehicle or otherwise. Ideally, the mat has a relatively flat upper surface and a relatively flat under or lower surface, such lower surface being adapted to be flush against the ground area where the mat is placed for the intended usage.

In general and summary, the mat will have some minimal degree of rigidity or hardness so that when one walks over the upper surface the mat will not overly compress or mush downwardly so as to interfere with a walking maneuver over such upper surface. Ideally and optimally the mat will have a longitudinally extending extent. Moreover, the upper surface should, but may not be critical to the invention, have a symmetrically formed upper surface, as viewed from an upper elevational view. This upper surface would optimally have two linear extending side borders or edges that are parallel to one another so that and by this physical feature the upper surface of the mat would appear to be mostly and substantially rectangular in nature to provide what would be a rectangularly shaped walkway and thus a longitudinally extending straight walkway from one end to the other. This upper surface walkway could have a longitudinally extending median stripe marker that would be designated or demarked as a medially extending line, that would be set off by a line of some color different than that of the upper surface of the mat or can be demarked by a slightly raised extending line or some other form of demarcation. This medial line would provide a longitudinal guide for walking a straight line.

It is contemplated however that the mat may be other than of rectangular shape and may be of such variant shapes as a curved member as viewed from above, such curved shape being adapted for even more intricate coordination testing, or may in fact have yet other physical shapes, all within the scope of the contemplated invention.

It is also contemplated that the mat structure may include, as an alternate embodiment, means to yield a leveling of the upper surface of the mat relative to a longitudinal position, all to overcome any complaint about the walking process being hampered by a lack of a level surface relative in a lateral degree of horizontal disposition, so that the walker would not be placing opposing feet at different levels. More directly stated, the most important aspect of the desired horizontal characteristic is the left-right horizontality as one walks on the mat. The longitudinal level aspect, i.e. end to end inclination or declination, is not as critical to the walking process as most individuals are usually adapted to walk in a coordinated manner on a straight-ahead upper or downward slope. On the other hand, in this perspective, it is much more difficult to conduct a coordinated walk when the left foot is at a higher position than the right foot, or vice versa.

Yet another aspect that can be additionally incorporated in the subject invention is electro-mechanical means to detect electronically, with possible connected computer read-out means, to detect and record the progress and moving positions of the feet of an individual over the mat surface relative to the mats marked boundaries. This latter aspect could include some computerized recording basis for law enforcement officers to supplement their oral testimony as to personal observations of the individual's walking abilities over the mat surface. Other variations can be implemented in this regard, including the integration of bubble mode level indicators located on various positions of the mat in order to ensure that the mat is positioned in a level position for usage.

H. DESCRIPTION OF PREFERRED EMBODIMENT OF SUBJECT INVENTION

In describing the preferred embodiment of the subject invention, there will be descriptions made of a few limited embodiments thereof. By description of any a few limited embodiments of the subject invention, it will not be considered as limiting the scope of the subject invention to such limited embodiment.

Figure 2:
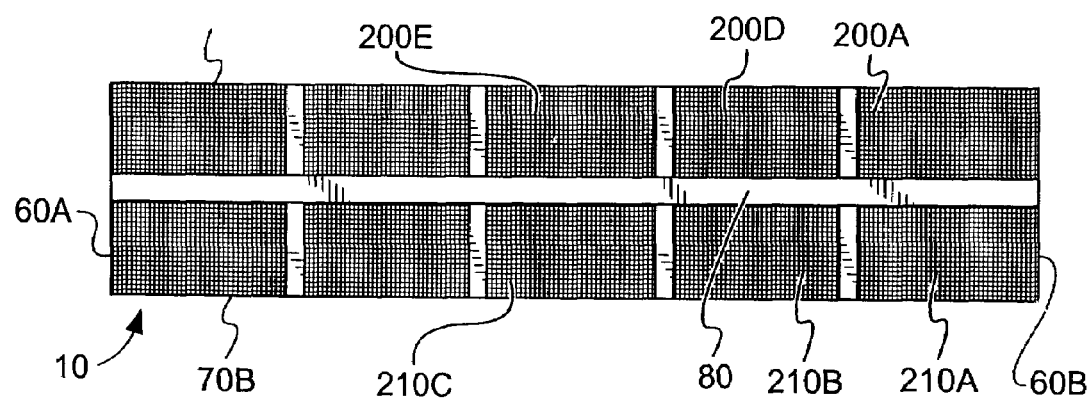
FIG. 2 is a top elevational view of another embodiment of the subject invention.
Figure 3:
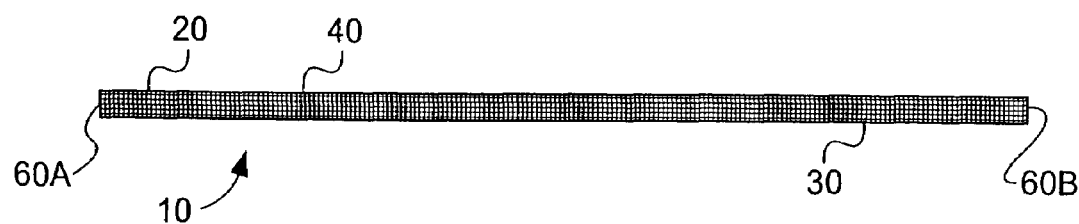
FIG. 3 is a side directional view of the embodiment shown in FIG. 1.

Reference is first had to FIGS. 1, 2 and 3 of the drawings in which the basic structural form of the preferred embodiment of the subject invention is shown. In particular, shown in such figure is a longitudinally extending portable mat member 10 which incorporates features of the subject invention. As shown, the mat member is a preferably longitudinally extending member having, when unfolded has a minimal longitudinal extent and has an upper surface 20 and lower surface 30, which surfaces are mutually opposing surfaces. It is preferred that the upper surface and lower surface both be longitudinally extending surfaces which are of equal and similar shape and size relative to one another. Most preferably, but not critically, is that the upper surface 20 be of rectangular configuration having an imaginary longitudinal central axis that will be a median line disposed longitudinally in a symmetrical manner in the middle of the upper surface extending from one end of such rectangular surface to the other, as more fully described below.

As can be seen in FIGS. 1, 2 and 3, the upper surface 20 and lower surface 30 of the mat 10 are separated by an intermediate cushioned member 40, which latter member optimally provides a cushioned composition that still yields some degree of rigidity and firmness that helps support the upper surface so that when one walks on the upper surface 20, he or she will not be inhibited in this walking process by undue sinking of the feet in the mat. This aspect is an obvious necessity for mats of such nature. To this purpose, any semi-rigid materials may be used as to the inner intermediate portion of the mat between the upper and lower surface so long as any need for portability of the mat are considered in this construction.

Attention is still directed to FIGS. 1, 2 and 3, and as can be seen the mat has an opposing end sides 60A and 60B, which end sides form the longitudinally opposing edges of the mat 10 and thus the longitudinally opposing edge boundaries of the upper surface 20. In similar fashion the lateral sides 70A and 70B of the mat 10 are opposing lateral sides of the mat, which opposing sides are of preferable equal length and shape, and when which form the lateral edge boundaries of the mat 10, and thus form the lateral side boundaries of the upper surface 20 of the mat.

As described above the mat 10 is formed as a rectangularly, longitudinally extending member, particularly viewing same from an upper elevational perspective view. In more technical parlance, the above described mat 10 structure is formed as a parallelopiped structure with even sides and edges, forming thusly a symmetrically and regularly shaped member. Stress is made in this respect, however, that the subject invention can be equally embodied in a mat structure of other configurations than that described above, and the indicated symmetry and regular and even shape of all sides and surfaces is not critical or limiting of the scope of this invention. For example, a curved mat can be utilized, as can be determined from subsequent descriptions or other variant mat shapes can be used so long as the mat has some upper surface over which the individual to be tested and observed can walk in full view of an observer.

In the preferred embodiment, the upper surface is provided with a median line 80 with some form of marking to make such line visually different than the rest of the upper surface 20 of mat 10, such demarcation of the line in the most simple format being a line colored white, as opposed, for example to a green colored upper surface. Whatever marking is used for such median line 80 on the upper surface of the mat 10 is not of a critical nature to implementation of the invention, as any form, color, shape or means to mark such line are considered within the scope and contemplation of this invention.

As stated and seen in the upper elevational view of FIG. 1, the longitudinally extending medial line 80 is preferably situated in the middle of the upper surface, but not essentially, but preferably extends down the exact middle of the upper surface 20 of the mat from the first edge 60A to the second edge 60B so that the upper surface 20 of the mat 10 is now divided into two separate sub rectangular portions 120A and 120B. On such upper surface 20, such separate rectangular portions 120A and 120B straddle each side of the medial line 80, as shown. Again, as indicated, it is not essential that the separate sub-rectangular portion 120A and 120B be of exact equal size and shape, however this attribute of symmetry and equality of size is preferred as can be surmised from the intended purpose of the subject invention. More specifically, it is the intention of this invention structure than an individual walk over the upper surface 20 of the mat 10 in a straightforward walking process whereby the individual moves his or her feet over the mat keeping each foot on opposing sub-rectangular portions 120A and 120B straddling the medial line 80.

Another potential attribute of the subject invention is that there can be distinctly marked laterally disposed outer boundary lines, not shown, along or near the lateral edges 70A and 70B of the mat. These lateral lines can help demark the outer area zone of the mat and more distinctly define the respective longitudinally extending half portions 120A and 120B of the upper surface of the mat 10, so that the individual tested will have distinctly marked half sections on which to place his or her respective right or left foot stepping along. In the preferred embodiment, it may be advisable to have the median line 80 colored with some form of bright flourescent substance not only to distinctly differentiate such line from the color of the mat but also to provide means for such lines to glow under darkened conditions. This latter aspect may minimize any potential complaints that the individual could not clearly see the median line 80 at night.

Another potential variation is to provide such distinct coloration of marking color for only the respective longitudinal half sections 120A and 120B. Other color or demarcation means may be used in conjunction with the subject invention in order to differentiate portions of the mat.

Still another variation that may be used in conjunction with the subject invention, as seen in FIG. 2, is to demark or somehow place marking means in the respective half sections 120A and 120B whereby each such half section 120A and 120B are further broken down into smaller successive sub-block portions 200A, 200B and 200C . . . and 201A, 210B, 210C . . . respectively for each half section 120A and 120B as can be seen in FIG. 2. In this embodiment, the sub-block sections 200A, 200B and 200C . . . and 210A, 210B, 210C, seen in FIG. 2, could be used for a walking maneuver whereby individuals would be requested to place his or her feet in such designated sub-blocks as they walk the line, with the understanding that the sub-blocks would be evenly spaced in a serial fashion along each sub-half, where all such sub-blocks would be spaced compatibly to a normal walking pace. Under such circumstances, the individual involved could be graded as to his or her ability to walk within designated sequence of blocks, such as placing the right foot in sub-block 200A, the left foot in sub-block 210B and then the right foot in sub-block 200C, and so on in such sequence.

Figure 4:
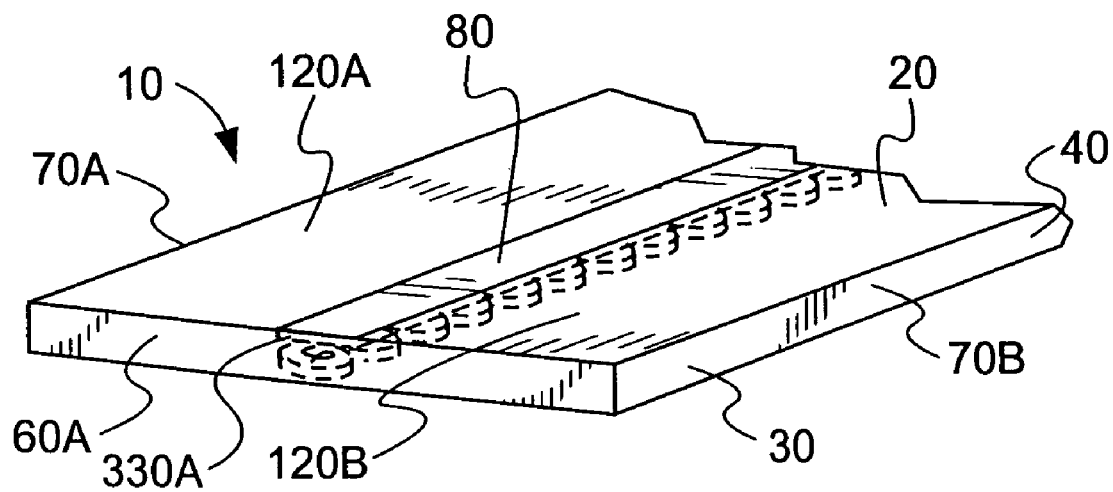
FIG. 4 is a perspective view of the subject invention showing spring registering means under the mat surface beneath the medial line.
Figure 5:
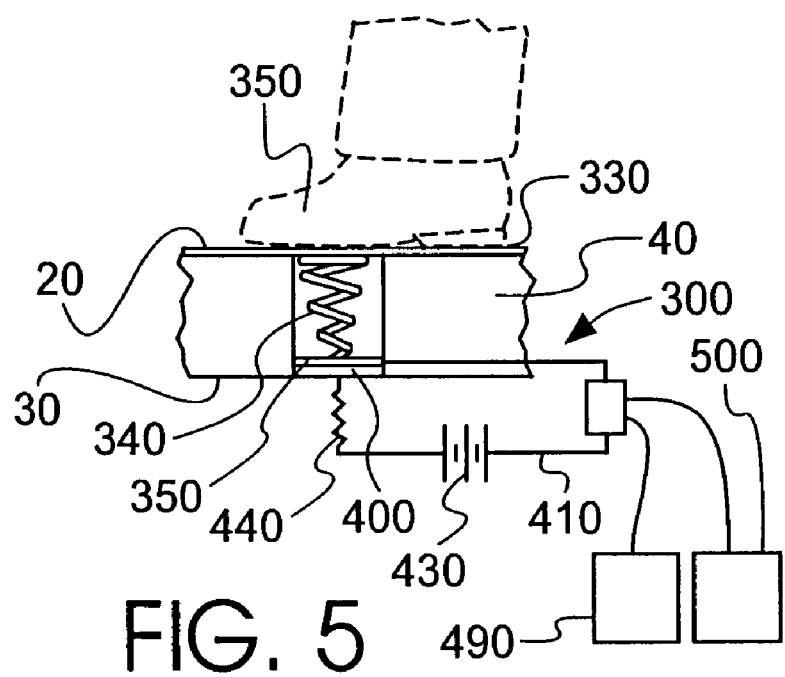
FIG. 5 is a schematic view of the pressure registering system represented in FIG. 4.

As seen in FIGS. 4 and 5a further alternate and optional embodiment could include electro-mechanical sensor means 300 disposed immediately beneath the medial line 80 portion. As further seen in FIGS. 4 and 5, such electro-mechanical means 300 could comprise in part a lateral longitudinally extending flat member 330 or other similar device disposed under the length of the medial line, being affixed within the inner composition of the mat and juxtaposed under the surface portion of the mat where the medial line 80 extends. Such electro-mechanical means 300 would include resilient means, such as a spring member 340 or a series of aligned spring members, which would permit the downward pressure movement on the flat member 330 whenever pressure of a predetermined amount is placed on top thereof, as graphically shown in FIG. 5. Thus when one walks on the mat upper surface 20 and places a foot portion 350 on a part of or on the medial line 80, this downwardly pressure would cause, for example as seen in FIG. 5, the flat member to depress downwardly, on a spring member 340 under the medial line. This downwardly compression would thereby cause the bottom of the spring 340 to also press downwardly to also compress a movable contact member 350 and touch a mating or contact member 400 to momentarily close a circuit 410 where is shown schematically in FIG. 5. This circuit 410 view schematically is comprised in part of a battery 430 which powers the circuit and a resister 440 along means in said circuit to signal a recording device. This recorder could include a bell 490, or be interconnected to a minicomputer 500 affixed within or next to the mat 10. Such minicomputer 500 would record an electric signal generated from a particular circuit and record the activation of circuit 400. Each demarcation line on the mat could optionally have its own sub-strata flat member 330 and each would have its own circuit in which to electrically sense a depression of the flat member by foot action, with each circuit having means to send signals to the central computer 500. It would be optimal for this purpose for each such subcircuit to provide uniquely differentiated signals to the minicomputer so that the minicomputer can record the differentiated signals to determine the precise line that has sensed foot pressure at a given time. In this regard, each circuit could provide uniquely differentiated voltage signals and utilize analog processing of the computer, or alternatively unique digital signals can be transmitted from any particular circuit for digital processing to the differentiate what areas of the mat are walked over.

In certain embodiments of the subject invention, it could be more feasible to place the pressure sensitive means in a strip that comprises the medial line 80 itself as placed over upper surface 20 of the mat 10. In this embodiment the line itself would have this pressure sensitive means, with electrical circuity that would respond electrically to the pressure placed in the medial 80 line, with electrical connecting means on each end of the line to interconnect the central minicomputer 500. For this purpose in this embodiment the line 80 would not simply be a painted or colored line it would be a self-contained unit as described above with some fastening or adhesion means on the under surface or otherwise to affix the line to the upper surface of the mat units proper demarcation point.

Figure 13:
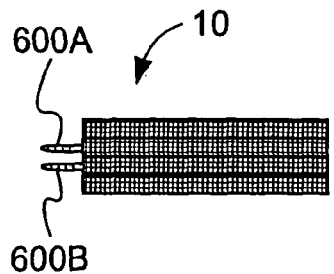
FIG. 13 is a fully folded mat structure as shown in FIG. 11, in folded arrangement.

In the embodiment shown in FIGS. 9, 10, 11, 12 and 13, handle members 600A and 600B are place on one side edge of the mat for handling the mat 10. The added feature is to have individual segmental portions of the mat flexibly affixed to one another in order to permit the mat to fold into a compact member as shown subsequently in FIGS. 10, 11, 12, and 13. Additionally, velcro fittings can be deployed on the mat surface to keep the mat folded into the compact position as shown in FIG. 13. Also a leveling indicator may be affixed to the mat to reveal how level the mat is when placed on the ground.

Figure 6:
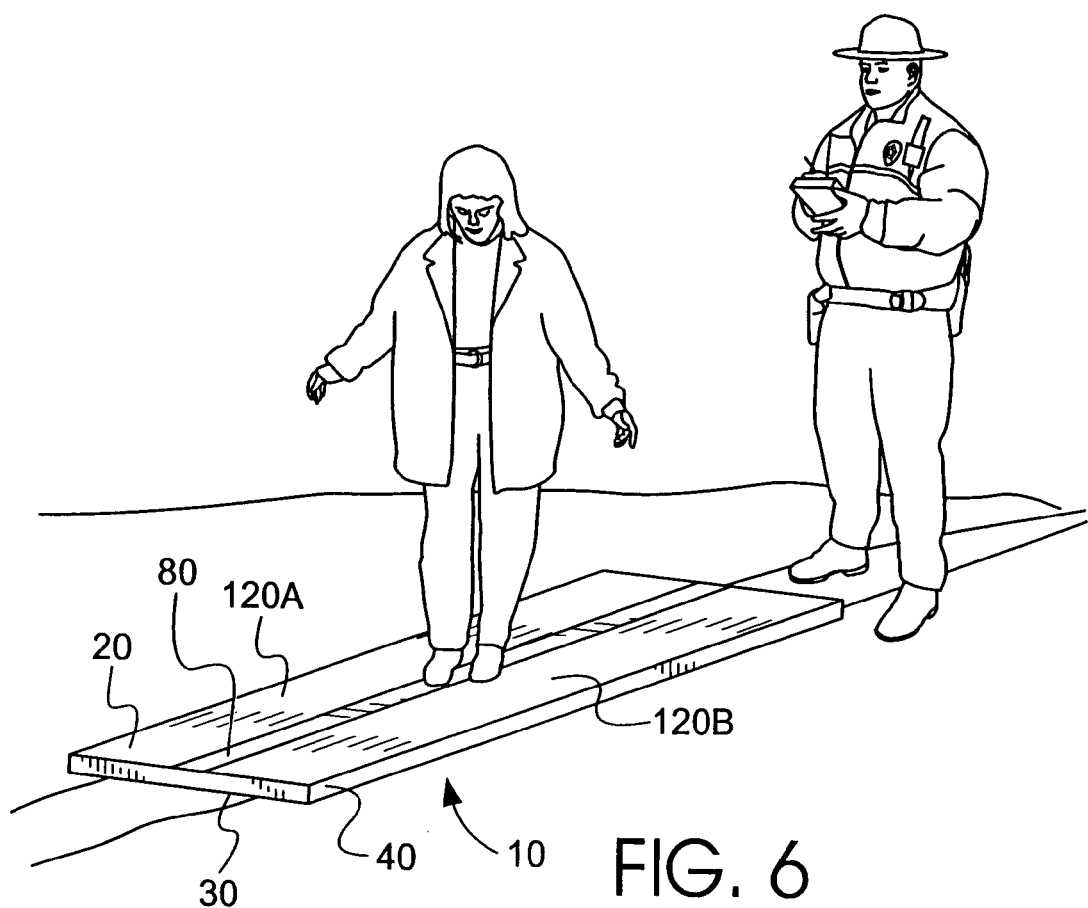
FIG. 6 is a perspective view of an individual walking on the upper surface of the mat structure shown in FIG. 1.
Figure 7:
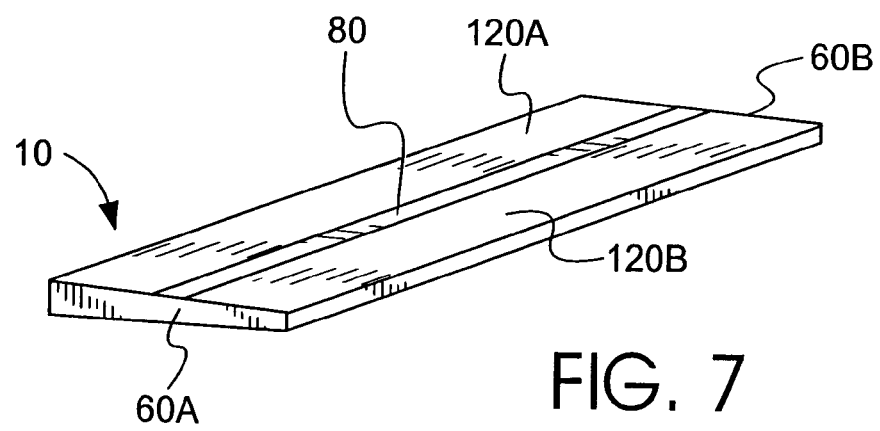
FIG. 7 is a perspective view of the basic embodiment shown in FIG. 1, however showing a variation wherein the one side edge is thicker than the other.
Figure 8:
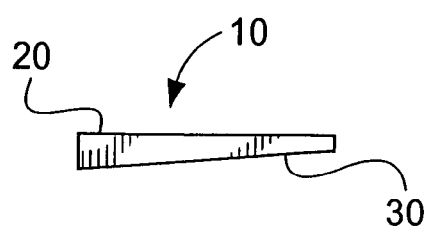
FIG. 8 is an end elevation view of the mat structure shown in FIG. 7.
Figure 9:
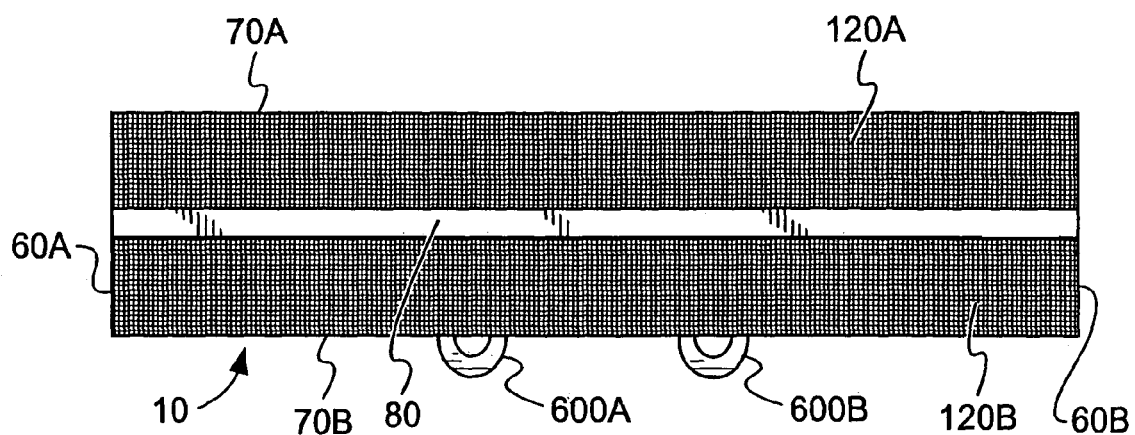
FIG. 9 is a top elevational view of the mat structure shown in FIG. 1, but with side handle members.
Figure 10:
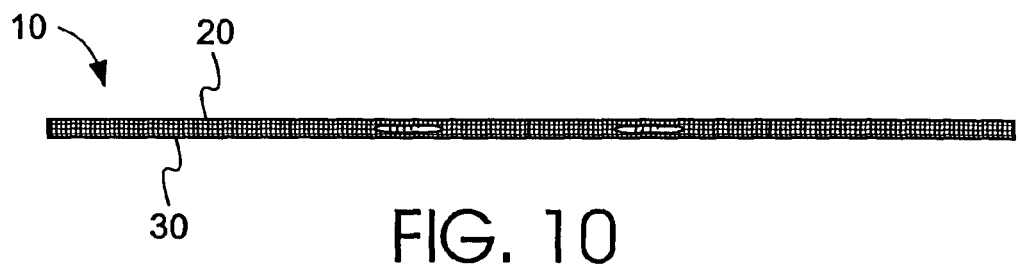
FIG. 10 is a side elevational view of the embodiment shown in FIG. 9.
Figure 11:
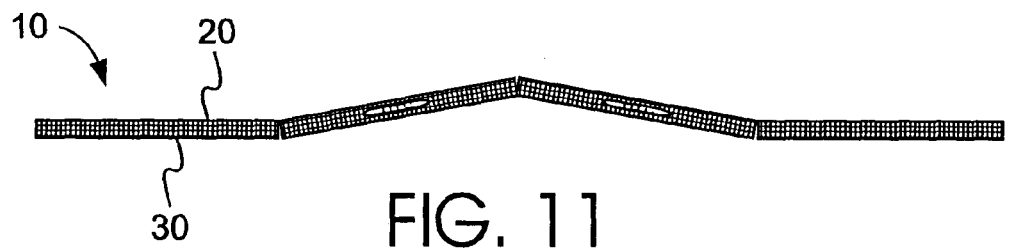
FIG. 11 is a side elevational view of a foldable mat structure embodying features of the subject invention.
Figure 12:
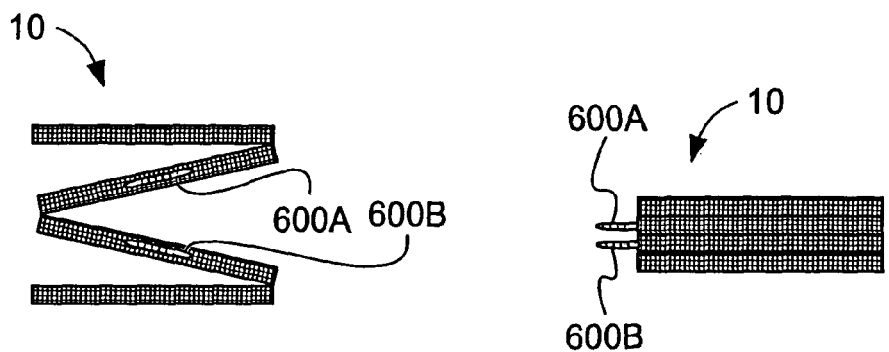
FIG. 12 is a partially folded mat structure as shown in FIG. 11.

In the embodiments shown in FIGS. 6, 7 and 8, one side edge of the mat is made 11 thicker than the other side edge. The purpose of this embodiment is to ensure that the upper surface of the mat is level on certain sloped berms or other surfaces.

The invention claimed is:

1. A portable mat member for guaging walking maneuvers and coordination maneuvers over the upper surface of such mat comprising:
    (a) a longitudinally extending mat member having an upper surface and a lower surface, said mat member having a first lateral edge and a second lateral edge, and said mat member having a first end edge and a second end edge, with said first lateral edge being thicker than said second lateral edge;
    (b) longitudinally extending marking means for guiding walking maneuvers over the surface of said mat member, said marking means extending longitudinally from said first end edge to said second end edge of said mat member wherein said marking means extend upwardly above said upper surface of said mat member and wherein said marking means has a luminous coating over a portion of said marking means;
    (c) electromechanical pressure sensor means disposed under said longitudinally extending marking means, said sensor means comprising a series of upright resilient spring members located in series under said longitudinally extending marking means, with each of said spring members being interconnected to a movable electromechanical contact member;
    (d) a mating electromechanical contact member to receive the downward structured contacting movement of said moveable electromechanical contact member which is pressed downwardly to the mating member said circuit having a therein a sound producing member to audibly signal said circuit being closed;
    (e) circuit means electronically interconnected to each of said mating eletromechanical contact members and having an electrically activated signalling means to detect activation of said electrical circuit by one or more of said mating electromechanical contact members being contacted by one of the said electromechanical pressure sensor means, said closed circuit means having integrated therein an electronically activated signalling device which is activated whenever said circuit is electrically activated by one or more of said electromechanical contact members.

* * * * *